United States Patent [19]

Zurbrügg et al.

[11] Patent Number: 5,219,174
[45] Date of Patent: Jun. 15, 1993

[54] DRILL CHUCK FOR A DRILL TO BE USED PARTICULARLY FOR SURGICAL PURPOSES

[75] Inventors: Andreas Zurbrügg, Basel; Jürg Schaufelberger, Aesch, both of Switzerland

[73] Assignee: Synthes (U.S.A.), Paoli, Pa.

[21] Appl. No.: 804,595

[22] Filed: Dec. 10, 1991

[30] Foreign Application Priority Data

Dec. 19, 1990 [CH] Switzerland ............ 04041/90

[51] Int. Cl.⁵ ............ B23B 31/107; A61B 17/16
[52] U.S. Cl. ............ 279/82; 279/158; 279/904; 433/128; 606/80
[58] Field of Search ............ 279/158, 76, 81, 82, 279/904, 905; 408/241 R; 606/79-81, 96-98; 433/127, 128

[56] References Cited

U.S. PATENT DOCUMENTS

| 4,661,062 | 4/1987 | Seigneurin | 433/128 |
| 4,808,185 | 2/1989 | Penenberg et al. | 623/20 |
| 4,850,344 | 7/1989 | Olerud et al. | 128/92 VD |
| 5,013,317 | 5/1991 | Cole et al. | 606/96 |
| 5,030,222 | 7/1991 | Calandruccio et al. | 606/79 X |
| 5,041,119 | 8/1991 | Frigg et al. | 606/96 |

FOREIGN PATENT DOCUMENTS

| 0339910 | 11/1989 | European Pat. Off. . | |
| 2918816 | 12/1979 | Fed. Rep. of Germany | 433/128 |
| 2834991 | 2/1980 | Fed. Rep. of Germany . | |
| 9013421 | 11/1990 | World Int. Prop. O. . | |

Primary Examiner—Steven C. Bishop
Attorney, Agent, or Firm—David Hoxie Faithfull & Hapgood

[57] ABSTRACT

A drill chuck is provided for surgical drilling machines in which the entire chuck is made of material permeable to X-radiation.

12 Claims, 1 Drawing Sheet

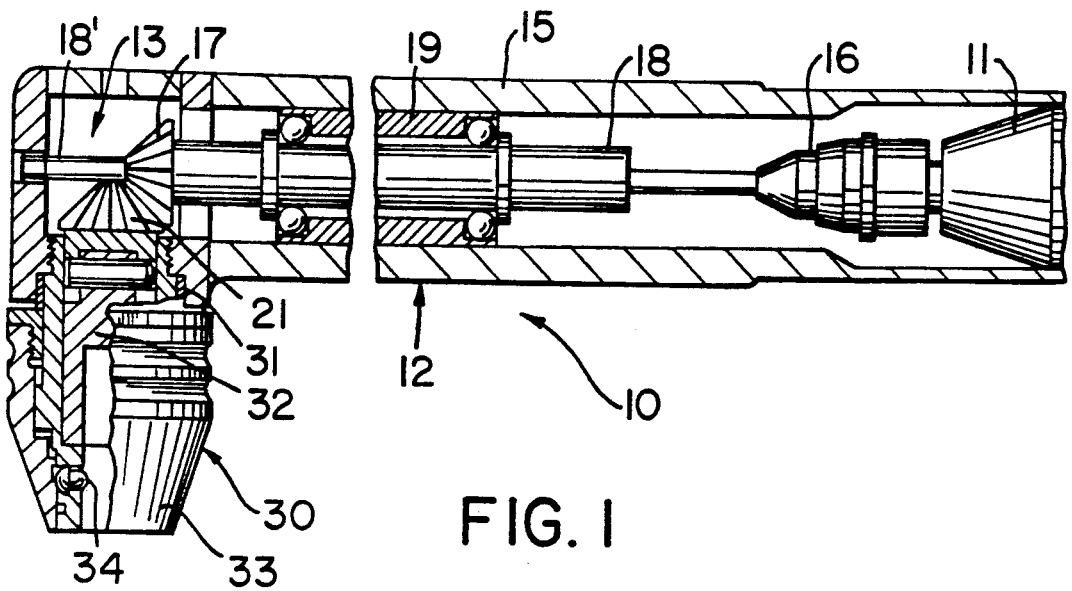
FIG. 1
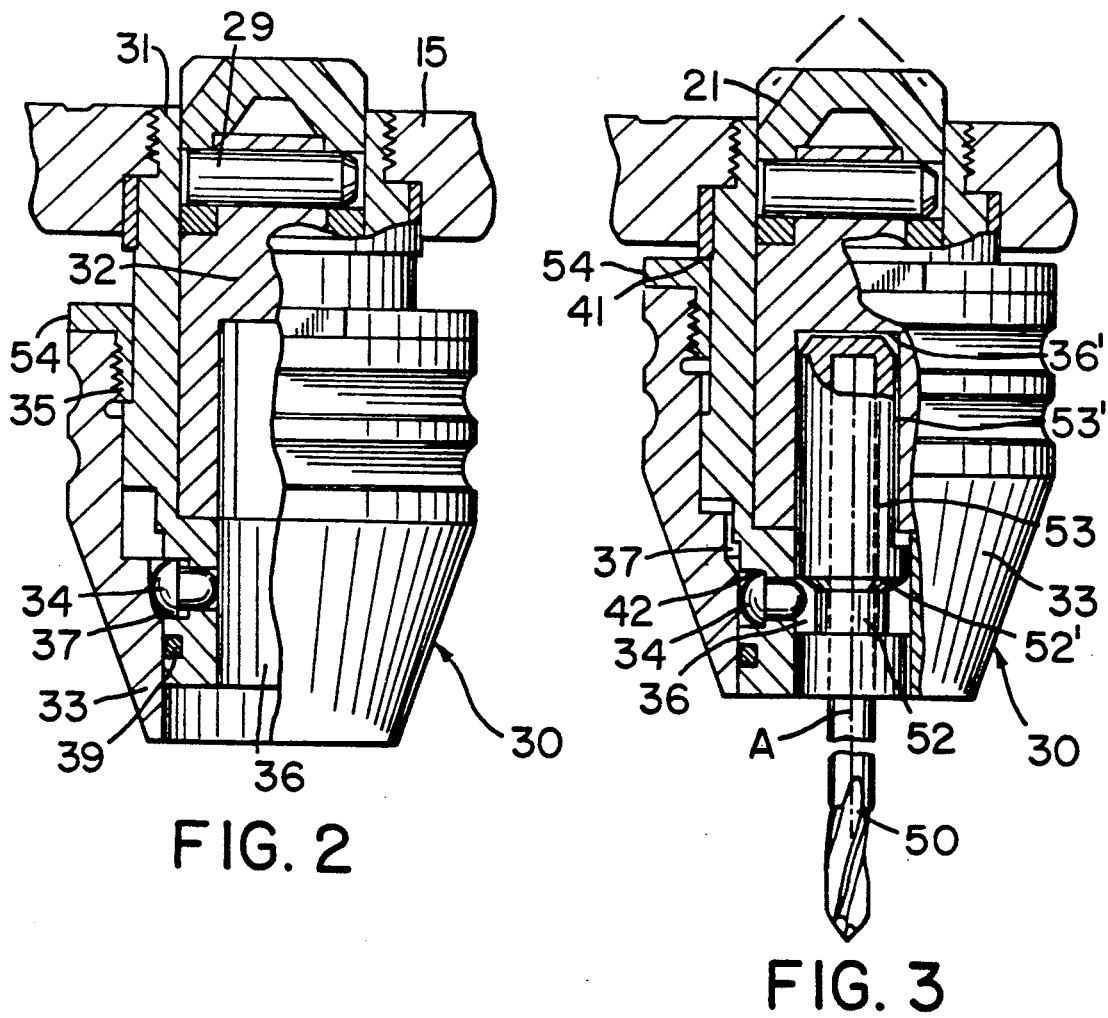
FIG. 2
FIG. 3

5,219,174

DRILL CHUCK FOR A DRILL TO BE USED PARTICULARLY FOR SURGICAL PURPOSES

FIELD OF THE INVENTION

This invention concerns a drill chuck for a drill that is to be used particularly for surgical purposes.

BACKGROUND OF THE INVENTION

A drilling device for surgical proposes is described in EPO application EP-A 90109556.2. It consists essentially of drive means, for example a compressed air turbine or an electrical motor, an angle attachment that can be connected with the drive means via a coupling, and a drill bit connected to the angular attachment. The angular attachment is made of a material that, at least as regards its components adjacent the drill bit, is X-ray permeable. This gives the surgeon unhindered image converter control, so that the operating field is visible to him on an X-ray screen without dark areas of any kind being created by the drilling device. This makes this device suitable for various osteosynthetic procedures, including the positioning of locking holes during intramedullary nailing. Particularly in intramedullary nailing, because of the anatomical-geometrical conditions, angle gear attachments of this type are used. The drill bit in this case can be connected, permanently or via a suitable coupling, with the drive shaft of the angle attachment. However, during an operation, it may be necessary to change one drill bit for another, for example one with a large diameter, as quickly as possible. Drilling devices according to this prior design are not well adapted to this.

SUMMARY OF THE INVENTION

In accordance with the present invention, a drill chuck is provided, especially for surgical purposes, which permits simple and rapid handling, particularly when a drill bit is being changed, while at the same time maintaining perfect and continuous screen monitoring of the drilling procedure by X-rays.

In accordance with the invention, the drill chuck is designed as a quick-change chuck, and is preferably made entirely of a material that is permeable by X-rays. The X-ray permeability creates optimum conditions for screen monitoring of the drilling by a surgeon, and also guarantees a very simple and rapid drill handling, especially when a drill bit is being changed.

The drill chuck, designed as a quick-change chuck, is preferably removably attached to an angle attachment of a drilling device, so that a drill bit can be changed or inserted easily. Advantageously, the chuck is connected to an angular attachment because for the aforementioned drilling purposes angular attachments are preferably used. However, the quick-change chuck can also be attached to a drill not having an angular attachment.

The quick-change chuck according to the invention consists of retaining means which holds a drill bit, a gripper sleeve that envelops the retaining means and can be slid in the direction of the drilling axis, and at least one locking pin that can be slid cross-wise to the drilling axis, which locking pin holds or releases the drill bit in response to longitudinal sliding of the gripper sleeve, whereby the desired ease of use is achieved to the maximum degree.

BRIEF DESCRIPTION OF THE DRAWINGS

Other details and advantages of the invention are explained in greater detail by means of the drawings in which:

FIG. 1 is a vertical section, partly in side elevation, of drilling device with a drill chuck according to the invention;

FIG. 2 is a vertical section, partly in side elevation, of the drill chuck of FIG. 1 in a position that releases the drill bit; and FIG. 3 is a vertical section, partly in side elevation, of the drill chuck of FIG. 1 in the position of holding the drill.

DETAILED DESCRIPTION OF THE INVENTION

The drilling device 10 shown in FIG. 1 consists essentially of a partially illustrated drive means 11, an angular attachment 12 having an angle gear 13 which angle gear 13 is rotationally connected with the drive 11, and a quick-change chuck 30, which is linked on the drive side to the angle gear 13. The drive means 11 can, for example, be an electric motor or a compressed air turbine, and it has a chuck 16 that is detachedly coupled with a drive shaft 18 of angle gear 13. By means of a bearing 19 that consists, for example, of two anti-friction bearings, the drive shaft 18 is rotationally held in a housing 15 of angle attachment 12, which housing is attached to drive 11. For stabilization purposes, drive shaft 18 is additionally supported at its front end 18' in housing 15. Shaft 18 has attached to its forward section a bevel gear 17, which engages a bevel gear 21 to form the angle gear 13, which is also housed in housing 15.

The driven-side bevel gear 21 is rotationally linked, by means of a pin 29, with a coupling shaft 32 connected to the drive shaft 18 at a 90° angle. This coupling shaft 32 is a component of the quick-change drill chuck 30 according to the invention. The drill chuck 30 consists of a retainer 31 permanently screwed to housing 15, a gripper sleeve 33 that envelops the retainer 31 and may be slid back and forth in the direction of drilling axis A, and three locking pins 34 positioned to slide transversely to drilling axis A and offset from each other at 120° angles. The coupling shaft 32 is rotationally housed in retainer 31, and together they form an opening 36 into which a drill bit 50 can be inserted. The quick-change chuck 30 is made entirely of a material that is permeable by x-rays. Materials such as polyetheretherketone (PEEK), polyamidimide (known, for example, under the name TORLON), and polyoxymethylene (POM) have in particular proven to be very suitable. Their advantage is that in addition to being permeable by x-rays they are also self lubricating and can be sterilized at temperatures up to 140° C. Composite plastics, preferably reinforced by fiber, cloth, or pellets, or special ceramic materials, can also be used.

FIG. 2 shows the quick-change chuck 30 in the position of having released a drill, and FIG. 3 shows the same chuck in a position of holding a drill 50. In the position of FIG. 2, the gripper sleeve 33 is slid over the retainer 31 to a stop 35 at the drill side of the chuck. The locking pins 34, positioned in the chuck 31 in such manner as to slide crossways to drill axis A, are thereupon in pushed-back position, that is, they do not extend into the opening 36 that accepts the drill 50. This is achieved by means of a guide track 37 inside gripper sleeve 33 and running in the direction of drill axis A which permits the locking pin 34 to move radially outward. For this particular embodiment, though only one is shown, there are three locking pins 34 on the circumference of the chuck 31, spaced circumferentially from one another at angles of 120° each. However, it is possible to use only a single pin, or more than three pins.

In FIG. 3 in which the quick-change chuck 30 holds the drill 50, the gripper sleeve 33 is pushed against a stop 41 at the drive side of the chuck. The locking pins 34 project into the opening 36, and thus into an annular groove 52 of a drill shank 53 in which the drill bit 50 is gripped. By means of the sliding of gripper sleeve 33, locking pin 34 is moved in the guide track 37 radially inward to a stop 42 in the retainer 31. The semi-spherical head of the locking pin 34 permits accurate guiding of the said pin in guide track 37. An annular groove 52 in drill shank 53 has a tapered groove surface 52', which is in contact with the rounded tip of locking pin 34, with drill shank 53 striking frontally against a rear frontal surface 36' in opening 36, whereupon drill bit 50 is fixed in its axial direction. Drill shank 53 further has a contact surface 53', and is thus held solidly in opening 36 inside coupling shaft 32 and is moved by said coupling shaft 32. In contrast to drill bit 50, drill shank 53 is made of a material that is permeable by x-rays, and thus the exact drill path can be determined and followed on a screen, for according to the invention, the components of the quick-change chuck 30 transmit the x-rays practically without any loss. On the other hand, for wear resistance, it is possible to make the locking pins 53 of a material not permeable by x-rays.

It should further be mentioned that gripper sleeve 33 consists of the sleeve proper as well as an additional ring 54 that grips the retainer 31, with the gripper sleeve 33 being screwed onto and secured by the ring 54. Between the sleeve and the retainer, on the end facing the drill, there is an O-ring 39 that acts as a seal and in particular as a stop when the gripper sleeve is slid.

The retainer and the coupling shaft housed in it may also consist of a single unit. This is then housed rotationally in housing 15 and rotationally connected with bevel gear 21. Consequently, the entire drill change chuck 30 rotates, whereas in the embodiment described it does not move, and only the coupling shaft 32 and drill bit 50 turn with shaft 53.

What is claimed is:

1. A quick-change drill chuck for use with surgical drilling machines, said entire chuck being made of material permeable to x-radiation and comprising drill bit retainer means having a central axis, a gripper sleeve surrounding said retainer means and adapted to slide over said retainer means in the axial direction and a locking pin positioned in the retaining means to slide transversely from a position in which it secures a drill bit in the retaining means to a position in which it permits a drill bit seated in said retainer means to be removed from the retainer means, said pin being moved from one of said positions to the other by sliding movement of the gripper sleeve.

2. The drill chuck claimed in claim 1 wherein the retainer means has a coupling shaft, rotatively seated therein, said shaft having a recess for receiving a drill bit at one end and gear means at its other end for attachment to said rotational drive means.

3. The drilling device claimed in claim 1 wherein said angle attachment has a housing and a drive shaft connected at one end to said drive means and at the other to a bevel gear and said drill chuck has drill bit retainer means comprising a coupling shaft having a recess for receiving a drill bit and a bevel gear engaging the bevel gear in said angle attachment at a 90° angle, said retainer means being detachably connected to the housing of said angle attachment.

4. The drilling device claimed in claim 3 wherein said chuck has a gripper sleeve surrounding said retainer means and adapted to slide over said retainer means in the axial direction and a looking pin positioned in the retaining means, and operable by said gripper sleeve to retain a drill bit in said retainer means.

5. The drill chuck claimed in claim 1, wherein the retainer means has drive side and drill side stops limiting the sliding movement of the gripper sleeve, and said gripper sleeve has a guide track to receive the locking pin when the gripper sleeve is in its drill side position.

6. The drill chuck claimed in claim 1 wherein the retaining means has drive side and drill side position stops, limiting the sliding movement of the gripper sleeve, wherein said chuck comprises three locking pins separated by 120° from one another, each of said pins having a rounded tip and a hemispherical head, said gripper sleeve having a guide track to receive the heads of said pins when said gripper sleeve is in the drive side position.

7. A drilling device for use in surgery comprising drive means, a drill bit and a quick-change chuck connected to said drive means for rotation by said drive means, said chuck having retainer means, a coupling shaft rotationally seated in said retainer means and having a recess for receiving a drill bit having a shaft and a gripper sleeve surrounding said retaining means, said retaining means having a plurality of pins, said gripper sleeve being slidable on said retainer means to move said pins into engagement with said drill shaft to retain said drill shaft and drill bit in said recess for rotation with said coupling shaft.

8. The drilling device claimed in claim 7 wherein said drill bit shaft has an annular groove to receive a pin for retaining said drill bit in said recess.

9. The drilling device claimed in claim 8 wherein there are three locking pins, said pins having rounded tips and hemispherical heads, said gripper sleeve having an annular groove for receiving the heads of said pins when said pins are not in engagement with said drill bit shaft, and the annular groove of said drill bit shaft having an oblique surface, contact of the locking pins with said surface pressing the drill shaft against the rear surface of the recess of said coupling shaft, thereby to limit axial movement of the drill bit.

10. The drilling device claimed in claim 7 wherein the drill bit is not permeable to x-radiation and is fixed in the drill bit shaft which is permeable to x-radiation.

11. The drilling device claimed in claim 7 wherein the drill bit shaft is retained in the recess on the coupling shaft by friction.

12. The drilling device claimed in claim 1 wherein the material permeable to x-radiation is selected from the group consisting of polyetheretherketones, polyamidimides, polyoxymethylenes and combinations thereof.

* * * * *